United States Patent
Hsu et al.

(10) Patent No.: US 7,655,128 B2
(45) Date of Patent: Feb. 2, 2010

(54) ELECTROCHEMICAL TEST STRIP

(75) Inventors: Yu-Sen Hsu, Hsinchu (TW); Ying Che Huang, Hsinchu (TW); Thomas Y.S. Shen, Hsinchu (TW)

(73) Assignee: Apex Biotechnology Corp., Hsinchu (CN)

( * ) Notice: Subject to any disclaimer, the term of this patent is extended or adjusted under 35 U.S.C. 154(b) by 421 days.

(21) Appl. No.: 11/640,886

(22) Filed: Dec. 19, 2006

(65) Prior Publication Data

US 2007/0144918 A1    Jun. 28, 2007

(30) Foreign Application Priority Data

Dec. 23, 2005    (TW)    ............................... 94146334 A

(51) Int. Cl.
*G01N 27/403*    (2006.01)
*G01N 27/327*    (2006.01)

(52) U.S. Cl. .................. 205/775; 204/400; 204/403.02; 205/777.5

(58) Field of Classification Search . 204/403.1–403.15; 205/777.5, 778, 792
See application file for complete search history.

(56) References Cited

U.S. PATENT DOCUMENTS 5,266,179 A * 11/1993 Nankai et al. ............... 204/401
5,582,697 A    12/1996 Ikeda et al. ............... 205/777.5
6,939,450 B2    9/2005 Karinka et al. ............ 204/409
2005/0023152 A1    2/2005 Surridge et al. ........... 205/775

FOREIGN PATENT DOCUMENTS

| EP | 0 359 831 B1 | 3/1989 |
| EP | 0 471 986 A2 | 7/1991 |
| EP | 0 537 761 A2 | 10/1992 |
| JP | 6-109688 | 9/1992 |
| TW | 200407542 | 11/2002 |

* cited by examiner

*Primary Examiner*—Alex Noguerola
(74) *Attorney, Agent, or Firm*—Stites & Harbison PLLC; Juan Carlos A. Marquez, Esq.

(57) ABSTRACT

An electrochemical test system comprising an electrochemical test strip capable of initiating an instrument, determining if it is inserted into a correct position of the instrument, a sample is injected into a reaction region of the electrochemical test strip, and the sample covers the reaction region properly. The electrochemical test strip includes an insulating substrate, an electrode system, and an insulating layer. The electrode system includes a resistor, a set of measurement electrodes which includes a reference electrode and a working electrode insulated from each other, and a set of identifying electrodes which includes first and second identifying electrodes connected through the resistor. A method for detecting a sample includes the steps of inserting the electrochemical test strip into a measurement instrument, providing the sample in the reaction region, and applying a voltage between the reference electrode and the working electrode, and measuring a current corresponding to the voltage.

16 Claims, 4 Drawing Sheets

ELECTROCHEMICAL TEST STRIP

FIELD OF INVENTION

The present invention generally relates to an electrochemical test strip, and more particularly, to an electrochemical test strip capable of initiating an instrument, determining if it is inserted into a correct position of the instrument, determining if a sample is injected into a reaction region of the electrochemical test strip, and determining if the sample covers the reaction region properly.

BACKGROUND OF THE INVENTION

The electrochemical test strips are widely employed in medical or biochemical test. The known electrochemical test strip has two electrodes for measuring the electrical characteristics of a sample after the sample being injected into a reaction region of the electrochemical test strip. However, in a such structure, the electrochemical test strip cannot determine if the sample already covers two electrodes, and even cannot determine if the sample is injected into the reaction region.

To solve the above-mentioned problem, U.S. Pat. No. 5,582,697 disclosed an electrochemical test strip with three electrodes. U.S. Pat. No. 5,582,697 added a third electrode in the reaction region, and the third electrode is disposed farther from an entry of the reaction region than the other two electrodes. After injecting sample, the current variation between the electrode nearest to the entry and the electrode farthest from the entry is detected to determine if the sample appropriately covers the electrodes. To detect the sample, the test strip has to be inserted into an instrument and then electrically connect with the instrument. However, the method disclosed in U.S. Pat. No. 5,582,697 is unable to determine if the test strip is inserted into the instrument correctly, and is unable to determine if the sample is injected into the reaction region until the sample covers most part of the reaction region.

Accordingly, it is advantageous to have an electrochemical test strip capable of determining if it is inserted into a correct position of the instrument and capable of testing the injection condition of the sample.

SUMMARY OF THE INVENTION

To solve the above-mentioned problems, the present invention provides an electrochemical test strip capable of assisting in inserting the test strip into a correct position of an instrument, determining if a sample being injected into a reaction region, and determining if the amount of sample being injected into the reaction region is sufficient.

According to an aspect of the present invention, an electrochemical test strip capable of testing injection condition of a sample is provided. The electrochemical test strip includes an insulating substrate, an electrode system formed on the insulating substrate, and an insulating layer formed on the electrode system. The electrode system includes a set of measurement electrodes, a set of identifying electrodes and a resistor, wherein the set of measurement electrodes includes a reference electrode and a working electrode insulated from each other, and the set of identifying electrode includes a first identifying electrode and a second identifying electrode connected with each other through the resistor. The insulating layer covers a part of the electrode system, wherein a part of the electrode system not covered by the insulating layer forms a reaction region with a supply port. When the sample is injected into the supply port of the reaction region, the sample reaches the set of measurement electrodes and the set of identifying electrodes in sequence.

According to another aspect of the present invention, an electrochemical test system is provided. The electrochemical test system includes the above-mentioned electrochemical test strip and a measurement instrument. The measurement instrument includes a switch module, an analog-digital converter, a processor, and an insertion detector. The switch module couples to the electrode system and is configured to selectively conduct an electrical connection between the electrode system and the measurement instrument. The analog-digital converter couples to the switch module. The processor couples to the analog-digital converter and the switch module, and is configured to control the switch module. The insertion detector couples to the switch module and the processor, and is configured to detect an electrical connection between the electrochemical test strip and the measurement instrument.

According to another aspect of the present invention, an electrochemical test system is provided. The electrochemical test system includes the above-mentioned electrochemical test strip, an initiating device, a voltage supply device, and a measurement device. The initiating device forms a loop by coupling to the electrochemical test strip. The voltage supply device is configured to provide a voltage between the electrodes. The measurement device is configured to measure an electrical variation between the first identify electrode and the second identify electrode, and an electrical variation between the reference electrode and the working electrode.

According to another aspect of the present invention, a method for detecting a sample using the above-mentioned electrochemical test strip is provided. The method includes the following steps: (a) inserting the electrochemical test strip into a measurement instrument to initiate the measurement instrument by forming a loop among the first identifying electrode, the resistor, the second identifying electrode, and the measurement instrument; (b) measuring a resistance between the first identifying electrode and the second identifying electrode to determine whether the electrochemical test strip is inserted into the measurement instrument properly; (c) providing the sample in the reaction region; (d) measuring an electrical variation between the reference electrode and the working electrode caused by the sample; (e) measuring an electrical variation between the first identifying electrode and the second identifying electrode; and (f) applying a voltage between the reference electrode and the working electrode, and measuring a current corresponding to the voltage.

The objectives, embodiments, features, and advantages of the invention will be apparent from the following more particular description of preferred embodiments and drawings of the invention.

BRIEF DESCRIPTION OF THE PICTURES

The foregoing aspects and many of the attendant advantages of this invention will become more readily appreciated as the same becomes better understood by reference to the following detailed description, when taken in conjunction with the accompanying pictures, wherein.

DETAILED DESCRIPTION OF THE INVENTION

The present invention directs to an electrochemical test strip and a method for using the same. The present invention will be described more fully hereinafter with reference to the FIGS. 1-4. However, the devices, elements, and methods in the following description are configured to illustrate the present invention, and should not be construed in a limiting sense.

Figure 1:
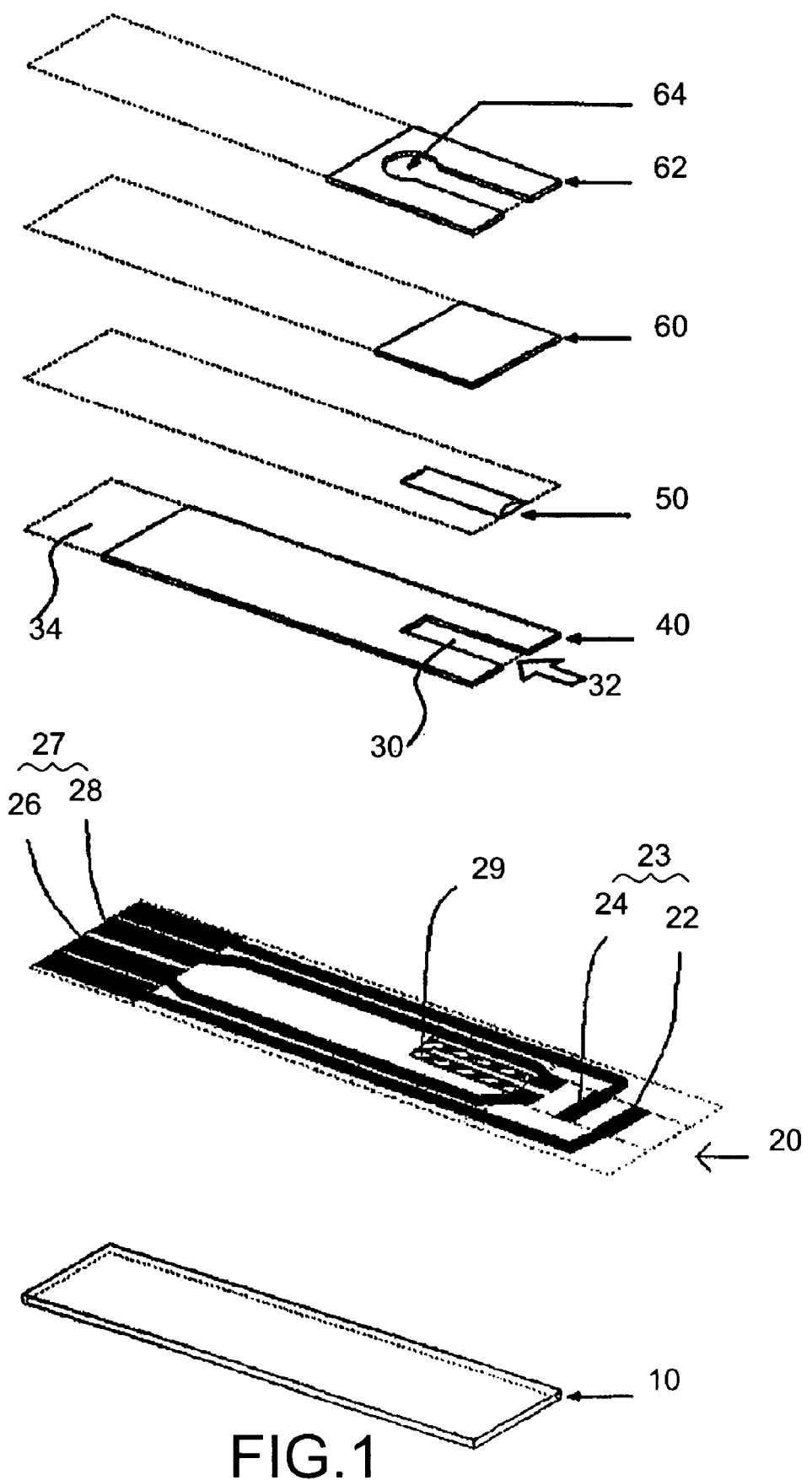
FIG. 1 shows a perspective view of an electrochemical test strip in accordance with an embodiment of the present invention.

FIG. 1 shows a perspective view of an electrochemical test strip in accordance with an embodiment of the present invention, in which the outline of the electrochemical test strip is plotted by dotted lines for comprehending the relative position among each element easily. The electrochemical test strip of the present invention includes an insulating substrate 10, an electrode system 20, an insulating layer 40, a hydrophilic layer 60, and a cover 62. The insulating layer 10 is electrically insulating and can be formed from a plate made of polyvinylchloride (PVC), glass fiber, polyester, bakelite, polyethylene terephthalate (PET), Polycarbonate (PC), polypropylene (PP), polyethylene (PE), polystyrene (PS), ceramic material or any other suitable material known in the art. The electrode system 20 includes a set of measurement electrodes 23, a set of identifying electrodes 27 and a resistor 29, wherein the set of measurement electrodes 23 includes a reference electrode 22 and a working electrode 24 insulated from each other, and the set of identifying electrode includes a first identifying electrode 26 and a second identifying electrode 28 connected with each other through the resistor 29. The material for the electrode system 20 can be any known conductive materials such as carbon paste, silver paste, copper paste, carbon/silver paste, or other similar material and the combination thereof. The insulating layer 40 covers a part of the electrode system 20, and a first part of the electrode system 20 not covered by the insulating layer 40 forms a reaction region 30 at one end for containing the sample and a second part of the electrode system 20 not covered by the insulating layer 40 forms a connection region 34 at the other end. The reaction region 30 has a supply port 32 for injecting the sample. The material of the insulating layer 40 includes but not limited to PVC insulating tape, PET insulating tape, thermal drying insulating paint or ultraviolet drying insulating paint. When the sample is injected into the supply port 32 of the reaction region 30, the sample reaches the set of measurement electrodes 23 and the set of identifying electrodes 27 of the electrode system 20 in sequence. The electrochemical test strip of the present invention further includes a reaction layer 50 disposed in the reaction region 30, which at least includes an oxidoreductases for reacting with the sample, and the type of the oxidoreductases will vary with the sample to be tested. The reaction layer 50 covers at least the set of measurement electrodes 23 in the reaction region 30, and, alternatively, the reaction layer 50 can also cover the set of identifying electrodes 27 in the reaction region 30. The hydrophilic layer 60 and the cover 62 are arranged to form a vent hole 34 for discharging air in the reaction region 30, which enhances the capillary effect and facilitates the injection of the sample to shorten the time of filling the reaction region 30 with the sample. The hydrophilic layer 60 can conduct the flowing direction of the sample and has the function of discharging air.

After the electrochemical test strip is inserted into a measurement instrument, a loop is formed among the first identifying electrode 26, the second identifying electrode 28, and the measurement instrument through the resistor 29, and then the measurement instrument is initiated. After the measurement instrument is initiated, a resistance between the first identifying electrode 26 and the second identifying electrode 28 can be measured and compared with the resistance of the resistor 29 to determine whether the electrochemical test strip is inserted into the measurement instrument properly. After providing the sample into the electrochemical test strip, an electrical variation between the reference electrode 22 and the working electrode 24 caused by the sample is measured to determine whether the sample is injected into the reaction region 30.

In the reaction region 30, since the set of identifying electrodes 27 are positioned farther from the supply port 32 than the set of measurement electrodes 23, the sample has to cover the set of measurement electrodes 23 before it reaches the set of identifying electrodes 27. In other words, one can determine if the sample covers the set of measurement electrodes 23 by determining if the sample reaches the set of identifying electrodes 27. Therefore, after determining that the sample is injected into the reaction region 30, an electrical variation between the first identifying electrode 26 and the second identifying electrode 28 can be measured to determine if the sample reaches the set of identifying electrodes 27. For example, the method for measuring the electrical variation may include the steps of providing a voltage between the first identifying electrode 26 and the second identifying electrode 28, and then observing if the resistance variation corresponds to the variation caused by the sample reaching the first identifying electrode 26 and the second identifying electrode 28. In the example of FIG. 1, the resistance between the first identifying electrode 26 and the second identifying electrode 28 is about the same as the resistance of the resistor 29 before the sample is added, and will become the resistance of parallel connection of the resistor 29 and the effective resistor of the sample after the sample is added.

After determining that the sample covers the reaction region 30 properly, the electrical measurement between the reference electrode 22 and the working electrode 24 can be performed, which mainly measures the current variation caused by the electrochemical reaction between the sample and the oxidoreductases of the reaction layer 50 in the reaction region 30.

Figures 2A, 2B, 2C:
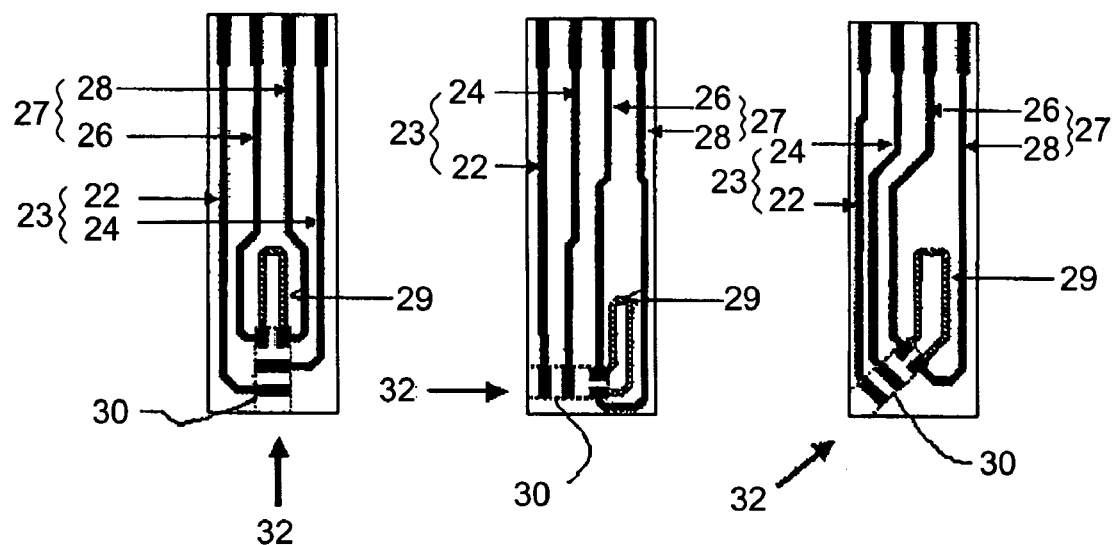
FIGS. 2A-2C illustrate three different electrode arrangements and configurations of reaction regions formed on the electrochemical test strip.

FIGS. 2A-2C illustrate three kinds of electrode arrangements and configurations of reaction region formed on the electrochemical test strip, wherein the reference electrode 22 and the working electrode 24 of the set of measurement electrodes 23 are insulated from each other, and the first identifying electrode 26 and the second identifying electrode 28 of the set of identifying electrodes 27 are separated from each other but connected through the resistor 29. In FIG. 2A, the supply port 32 of the reaction region 30 is on the underside. In FIG. 2B, the supply port 32 of the reaction region 30 is on the left side. In FIG. 2C, the supply port 32 of the reaction region 30 is on the underside left corner. As illustrated in FIGS. 2A-2C, the set of measurement electrodes 23 and the set of identifying electrodes 27 are arranged in sequence from a supply port 32 of the reaction region 30. Actually, as long as the electrodes in the reaction region 30 are arranged in the order described above and insulated from one another, the present invention does not limit the arrangement of the electrodes and the configuration of the reaction region 30.

Figure 3:
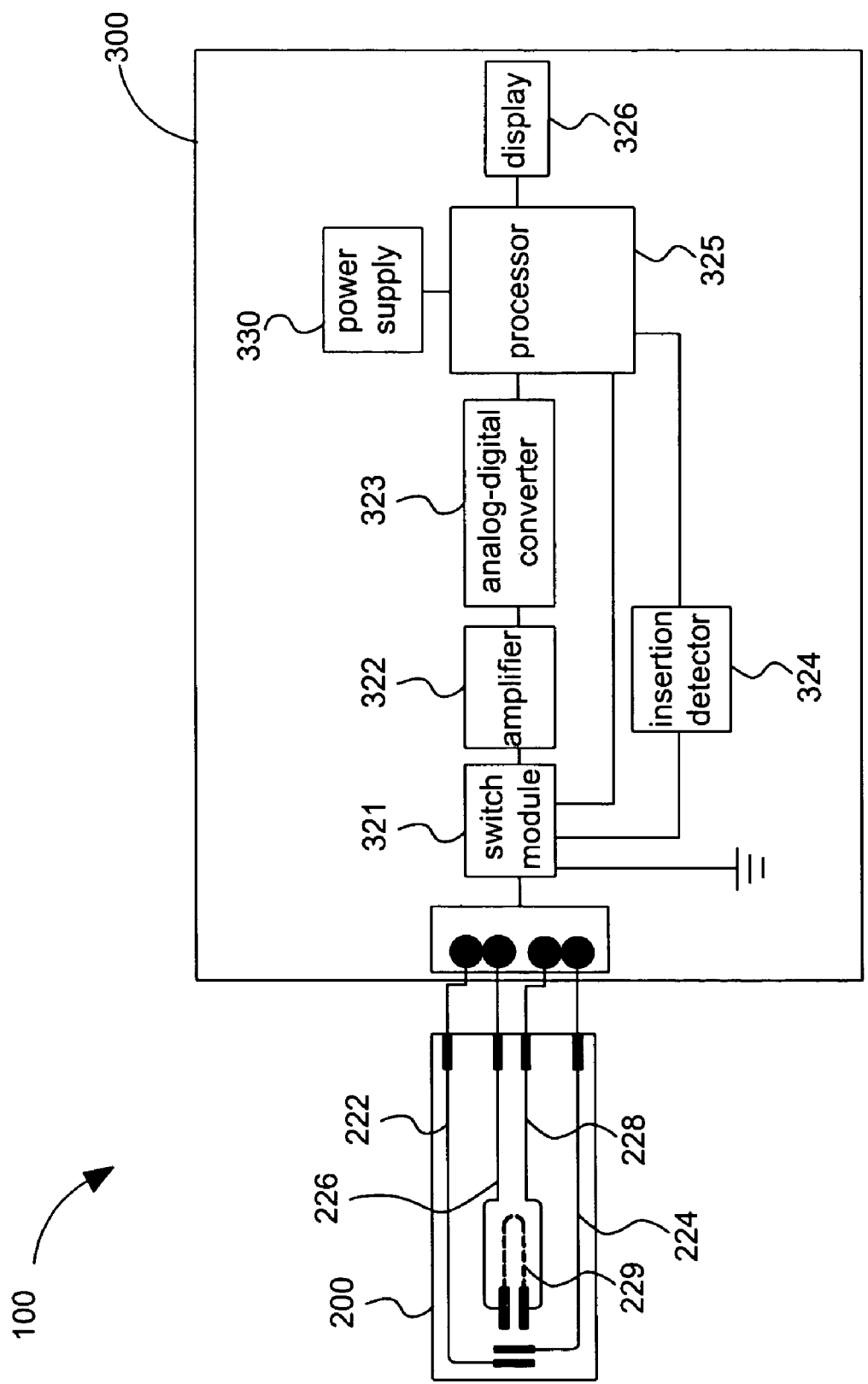
FIG. 3 shows a block diagram of a electrochemical test system in accordance with an embodiment of the present invention.

FIG. 3 shows a block diagram of a electrochemical test system 100 in accordance with an embodiment of the present invention, which includes an electrochemical test strip 200 of the present invention and a measurement instrument 300. The measurement instrument 300 includes connector 320 for external connection, a switch module 321, an amplifier 322, an analog-digital converter 323, an insertion detector 324, and a processor 325. The reference electrode 222, the working electrode 224, the first identifying electrode 226, and the second identifying electrode 228 of the electrochemical test strip 200 electrically connect to the measurement instrument 300 through the connector 320. The switch module 321 is configured to selectively connect the electrodes of the electrochemical test strip 200 to the ground point or to the circuits in the measurement instrument 300. The measurement instrument 300 further includes a display 326 for displaying the measurement result and a power supply 330 for providing power. In another embodiment of the present invention, the display 326 and the power supply 330 can be external devices, not included in the measurement instrument 300.

When the electrochemical test strip 200 connects with the connector 320, a loop is formed among the first identifying electrode 226, the resistor 229, the second identifying electrode 229, the connector 320, the switch module 321 and the insertion detector 324, whereby a signal is transmitted to the processor 325 to initiate the measurement instrument 300. The insertion detector 324 can be a known power-on circuit which is an open circuit before connecting with the test strip 200, and becomes a loop after connecting with the test strip 200. For example, the insertion detector 324 can include a diode or a transistor that will be turned on after the insertion of the test strip 200, and the caused voltage variation of the end point of the diode or the transistor can initiate the measurement instrument 300. However, in some situations, other unexpected factors may also initiate the measurement instrument 300. Therefore, the processor 325 can determine if the electrochemical test strip 200 connects with the connector 320 properly by providing a voltage between the first identifying electrode 226 and the second identifying electrode 228 after the measurement instrument 300 is initiated, and then measuring the resistance value and comparing it with the resistor 229.

After determining that the electrochemical test strip 200 is connected with the connector 320 properly, the processor 325 then provides a voltage between the reference electrode 222 and the working electrode 224. The resistance between the reference electrode 222 and the working electrode 224 will change after the sample is injected into the reaction region of the electrochemical test strip 200. Generally, the resistance is reduced because the sample connects the reference electrode 222 and the working electrode 224. Next, the resistance variation is digitalized by the amplifier 322 and the analog-digital converter 323 and then transmitted to the processor 325, and it allows the processor 325 to determine if the sample is injected into the reaction region.

After determining that the sample is injected into the reaction region, the distribution of the sample in the reaction region can be detected. According to an embodiment of the present invention, the processor 325 provides a voltage between the first identifying electrode 226 and the second identifying electrode 228 after determining that the sample is injected into the reaction region. Once the sample reaches the first identifying electrode 226 and the second identifying electrode 228 positioned at the far end of the reaction region, the processor 325 can determine that the sample covers the reaction region appropriately if there is a sufficient current variation being detected.

After determining that the sample covers the reaction region properly (i.e. the sample covers the reference electrode 222 and working electrode 224 completely), the processor 325 applies a voltage between the reference electrode 222 and the working electrode 224, and measures a current variation caused by the electrochemical reaction of the sample between the reference electrode 222 and the working electrode 224 via the amplifier 322 and the analog-digital converter 323.

Figure 4:
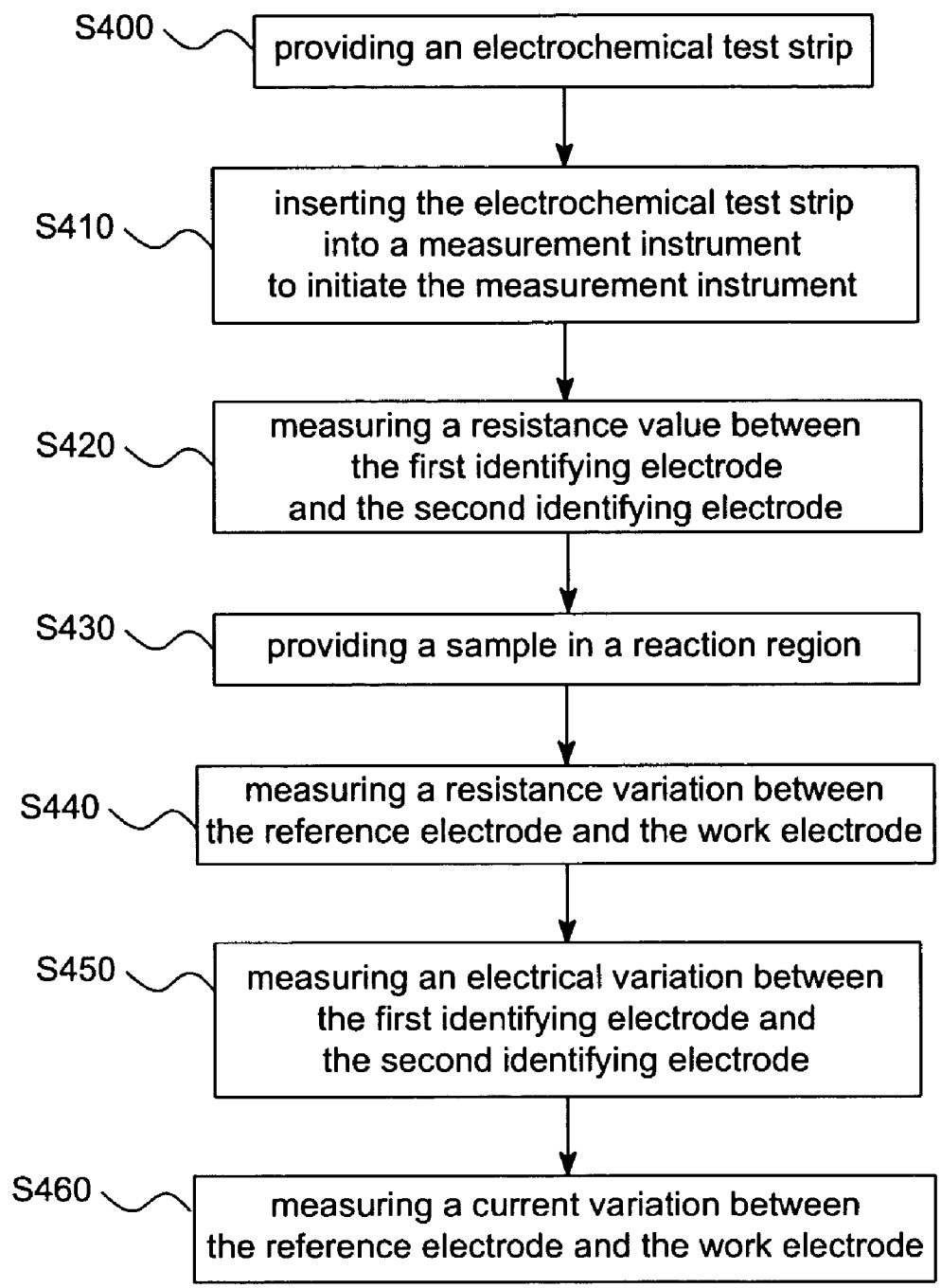
FIG. 4 is a flowchart showing the procedure of testing a sample by using an electrochemical test strip of the present invention.

FIG. 4 is a flowchart showing the procedure of testing a sample by using an electrochemical test strip of the present invention. First, in step S400, the electrochemical test strip of the present invention is provided. As described above, the test strip includes four electrodes insulated from one another: a reference electrode, a working electrode, a first identifying electrode, and a second identifying electrode, wherein the first identifying electrode and the second identifying electrode connect with each other through a resistor. In step S410, the electrochemical test strip is inserted into a measurement instrument to initiate the measurement instrument. After the instrument is initiated, in step S420, a resistance between the first identifying electrode and the second identifying electrode is measured. If the resistance corresponds to an expecting value, the procedure proceeds to step S430, and a sample is provided in a reaction region of the electrochemical test strip. Next, in step S440, a resistance variation between the reference electrode and the working electrode is measured, and it is indicated that the sample is injected into the reaction region if the resistance variation corresponds to an expecting value. After determining that the sample is injected into the reaction region properly, the procedure proceeds to step S450. In step S450, an electrical variation between the first identifying electrode and the second identifying electrode is measured, and it is indicated that the sample covers the reaction region properly if the electrical variation corresponds to an expecting value. For example, if the resistance has a sufficient variation compared with the resistance measured in step S420, it is determined that the sample covers the reaction region. Next, in step S460, the current variation between the reference electrode and the working electrode is measured for the test of the characteristics of the sample.

Although the specific embodiments of the present invention have been illustrated and described, it is to be understood that the invention is not limited to those embodiments. One skilled in the art may make various modifications without departing from the scope or spirit of the invention.

The present invention relates to an electrochemical test system that uses an electrochemical test strip capable of initiating an instrument, determining if it is inserted into a correct position of the instrument, determining if a sample is injected into a reaction region of the electrochemical test strip, and determining if the sample covers the reaction region properly. The electrochemical test strip includes an insulating substrate, an electrode system, and an insulating layer. The electrode system includes a set of measurement electrodes, a set of identifying electrodes and a resistor, wherein the set of measurement electrodes includes a reference electrode and a working electrode insulated from each other, and the set of identifying electrode includes first and second identifying electrodes connected through the resistor. A method for detecting a sample includes the steps of inserting the electrochemical test strip into a measurement instrument, measuring a resistance between the first and second identifying electrodes to determine whether the electrochemical test strip is inserted into the measurement instrument properly; providing the sample in the reaction region; measuring an electrical variation between the reference electrode and the working electrode caused by the sample; measuring an electrical variation between the first and second identifying electrodes; and applying a voltage between the reference electrode and the working electrode, and measuring a current corresponding to the voltage.

The invention claimed is:

1. An electrochemical test strip capable of testing injection condition of a sample, the electrochemical test strip comprising:
   an insulating substrate;
   an electrode system formed on the insulating substrate, the electrode system including a set of measurement electrodes, a set of identifying electrodes and a resistor having a predetermined resistance value, wherein the set of measurement electrodes comprises a reference electrode and a working electrode insulated from each other, and the set of identifying electrodes comprises a first identifying electrode and a second identifying electrode connected with each other through the resistor; and
   an insulating layer covering a part of the electrode system, wherein a part of the electrode system not covered by the insulating layer forms a reaction region with a supply port;
   wherein when the sample is injected into the supply port of the reaction region, the sample reaches the set of measurement electrodes and the set of identifying electrodes in sequence.

2. The electrochemical test strip of claim 1, further comprising a cover disposed on the insulating layer, the cover comprising a vent hole for discharging air in the reaction region.

3. The electrochemical test strip of claim 1, further comprising a reaction layer disposed on the reaction region, wherein the reaction layer comprises an oxidoreductases.

4. The electrochemical test strip of claim 3, wherein the reaction layer covers at least the set of measurement electrodes.

5. A method for detecting a sample using the electrochemical test strip of claim 1, comprising:
   (a) inserting the electrochemical test strip into a measurement instrument to initiate the measurement instrument by forming a loop among the first identifying electrode, the resistor, the second identifying electrode, and the measurement instrument;
   (b) providing the sample in the electrochemical test strip; and
   (c) applying a voltage between the reference electrode and the working electrode, and measuring a current corresponding to the voltage.

6. The method of claim 5, further comprising the following step between the step (a) and the step (b):
   (a1) measuring a resistance between the first identifying electrode and the second identifying electrode to determine whether the electrochemical test strip is inserted into the measurement instrument properly.

7. The method of claim 5, further comprising the following step between the step (b) and the step (c):
   (b1) measuring an electrical variation between the reference electrode and the working electrode caused by the sample to determine whether the sample is injected into the reaction region.

8. The method of claim 5, further comprising the following step between the step (b) and the step (c):
   (b2) measuring an electrical variation between the first identifying electrode and the second identifying electrode to determine whether the sample covers the reference electrode and the working electrode.

9. The method of claim 5, wherein the loop causes a voltage variation in an anode of a diode by turning on the diode, and the voltage variation initiates the measurement instrument.

10. The method of claim 5, wherein the loop cause a voltage variation in a collector of a transistor by turning on the transistor to, and the voltage variation initiates the measurement instrument.

11. An electrochemical test system, comprising:
    the electrochemical test strip of claim 1; and
    a measurement instrument, comprising: a switch module, coupled to the electrode system and configured to selectively conduct an electrical connection between the electrode system and the measurement instrument; an analog-digital converter coupled to the switch module; a processor coupled to the analog-digital converter and the switch module, the processor configured to control the switch module; and an insertion detector coupled to the switch module and the processor, the insertion detector configured to detect an electrical connection between the electrochemical test strip and the measurement instrument.

12. The electrochemical test system of claim 11, wherein an electrical variation between the reference electrode and the working electrode caused by the injection of the sample is transmitted to the processor through the analog-digital converter.

13. The electrochemical test system of claim 11, wherein the processor applies a voltage between the first identifying electrode and the second identifying electrode after the sample is injected into the reaction region of the electrochemical test strip to detect an electrical variation between the first identifying electrode and the second identifying electrode.

14. The electrochemical test system of claim 11, wherein the processor applies a voltage between the reference voltage and the working electrode after the sample is injected into the reaction region and contacts with the first and the second identifying electrode, and a current variation between the reference electrode and working electrode is obtained through the analog-digital converter.

15. The electrochemical test system of claim 11, wherein the measurement instrument further comprises a display coupled to the processor and configured to display an electrical variation of the electrode system.

16. An electrochemical test system, comprising:
    the electrochemical test strip of claim 1; and
    an initiating device forming a loop by coupling to the electrochemical test strip; a voltage supply device configured to provide a voltage among the electrodes; and a measurement device configured to measure an electrical variation between the first identify electrode and the second identify electrode, and an electrical variation between the reference electrode and the working electrode.

* * * * *

UNITED STATES PATENT AND TRADEMARK OFFICE
CERTIFICATE OF CORRECTION

PATENT NO. : 7,655,128 B2 Page 1 of 1
APPLICATION NO. : 11/640886
DATED : February 2, 2010
INVENTOR(S) : Hsu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 466 days.

Signed and Sealed this

Twenty-third Day of November, 2010

David J. Kappos
*Director of the United States Patent and Trademark Office*